US011446054B2

(12) United States Patent
Quek

(10) Patent No.: US 11,446,054 B2
(45) Date of Patent: Sep. 20, 2022

(54) APPARATUS FOR DETACHING SURGICAL BLADES

(71) Applicant: Aunex Pty Ltd, Stafford Heights (AU)

(72) Inventor: Kim Sia Quek, Stafford Heights (AU)

(73) Assignee: AUNEX PTY LTD., Stafford Heights (AU)

( * ) Notice: Subject to any disclaimer, the term of this patent is extended or adjusted under 35 U.S.C. 154(b) by 532 days.

(21) Appl. No.: 16/464,715

(22) PCT Filed: Feb. 14, 2018

(86) PCT No.: PCT/AU2018/050115
§ 371 (c)(1),
(2) Date: May 29, 2019

(87) PCT Pub. No.: WO2018/148793
PCT Pub. Date: Aug. 23, 2018

(65) Prior Publication Data
US 2019/0307481 A1 Oct. 10, 2019

(30) Foreign Application Priority Data
Feb. 15, 2017 (AU) .............................. 2017900477

(51) Int. Cl.
*A61B 17/3217* (2006.01)
*A61B 17/3213* (2006.01)
(Continued)

(52) U.S. Cl.
CPC ...... *A61B 17/3213* (2013.01); *A61B 17/3217* (2013.01); *A61B 50/362* (2016.02); *B65D 25/10* (2013.01); *B65D 83/10* (2013.01)

(58) Field of Classification Search
CPC .. A45D 27/225; A45D 27/24; A61B 17/3217; A61B 50/3001; A61B 50/36; A61B 50/362; B65D 25/10
(Continued)

(56) References Cited

U.S. PATENT DOCUMENTS 4,120,397 A    10/1978 Neumann
4,903,390 A *   2/1990 Vidal ................. A61B 17/3217
                                                    206/355

(Continued)

FOREIGN PATENT DOCUMENTS

CN    1777398 A    5/2006
RU    2144334 C1   1/2000
(Continued)

*Primary Examiner* — King M Chu
(74) *Attorney, Agent, or Firm* — Barlow, Josephs & Holmes, Ltd.

(57) ABSTRACT

An apparatus for detaching a blade from a scalpel handle is provided. The blade has a cutting portion and a heel portion and is removably mounted on a tang of the scalpel handle. The apparatus has a flexible blade detachment member with a stepped portion for engaging the heel of the blade as the handle is withdrawn and a leading angled portion. A backing member is provided with the detachment member being arranged adjacent the backing member so that during use the detachment member flexes in only one direction, away from the mounting tang in response to force applied by the handle to the leading angled portion thereby causing the blade and the handle to be separated and detached relative to each other. Upon withdrawing the tang from the opening, the stepped portion engages the heel of the blade resulting in detachment of the blade from the tang.

17 Claims, 16 Drawing Sheets

(51) Int. Cl.
  *A61B 50/36* (2016.01)
  *B65D 25/10* (2006.01)
  *B65D 83/10* (2006.01)

(58) Field of Classification Search
  USPC .......................................... 206/355, 359, 370
  See application file for complete search history.

(56) References Cited

U.S. PATENT DOCUMENTS 5,361,902 A    11/1994  Abidin et al.
5,699,908 A  * 12/1997  Frye .................. A61B 17/3217
                                                          206/355

FOREIGN PATENT DOCUMENTS

| WO | WO 1996/007363 | 3/1996 | |
|---|---|---|---|
| WO | WO 2004/093706 | 11/2004 | |
| WO | WO-2004093706 A1 * | 11/2004 | ......... A61B 17/3217 |

* cited by examiner

APPARATUS FOR DETACHING SURGICAL BLADES

TECHNICAL FIELD

The present invention relates generally to apparatus, devices, tools and systems directed to removing, used disposable surgical scalpel blades from scalpel handles and safely disposing of such contaminated blades.

BACKGROUND

Any references to methods, apparatus or documents of the prior art are not to be taken as constituting any evidence or admission that they formed, or form part of the common general knowledge.

It is known that modern surgical scalpel blades are disposable, and are designed to fit a reusable handle to form a surgical knife. FIGS. 1 and 1A illustrate a commercially available surgical knife 50 which comprises a reusable handle 10 and disposable blade 20. The surgical blade 20 comprises a sharpened tip 22 and cutting edge 24 at the forward portion of the blade and a shank 23 extending to the rear portion 21 of the blade 20 which forms the heel 25 of the blade 20. The blade 20 is formed with a central elongate slot 26. Shoulders 29 of the central slot 26 extend between a wider trailing slot portion 27 and narrower leading portion 39 of the slot 26 act as detents.

The scalpel handle 10 (shown in part) has an elongated boss, or tang 12, that is received into the central elongate slot 26 of the blade 20. The tang 12 has a region 13 of reduced thickness, with a forward-facing shoulder 14 located at the rear portion of the tang 12 where it attaches to the scalpel handle 10. The front 19 of the tang 12 is typically rounded, and the shoulder 14 of the reduced-thickness region is also typically rounded. The tang 12 comprises a lip 16 having a relatively greater thickness when compared with the shoulder 14 and is provided with a groove 17 extending around the lip 16. Whilst, FIGS. 1 and 2 illustrate a specific type of scalpel blade, it is known that scalpel blades can have many other shapes and sizes.

In order to mount a disposable scalpel blade 20 to handle 10, the front end 19 of the tang 12 is inserted into the trailing, wider part 27 of the scalpel blade's elongate slot 26 and pushed forward so that the narrow portion 39 of the scalpel blade slot 26 slides in the tang's grooves 17 until the rear edge 41 of the scalpel blade's slot 26 clears the rear of the lip 16 of the tang 12 so that the rear portion 21 of the scalpel blade 20 can then flatten, or snap, down against the reduced thickness region 13 of the tang thereby locking the blade 20 to the scalpel handle 10. In this position the rear heel portion 25 of the scalpel blade 20 locates against or close to the shoulder 14 which thus serves as a blade-retaining projection. The scalpel blade 20 is held from moving further backwards on the tang 12 by the detents 29 of the elongate slot of the blade 20 which abut the rearward ends of the groove 17 of tang 12.

To remove the scalpel blade 20 from the scalpel handle's tang 12, the heel portion 25 of the blade 20 must be brought away from a shoulder portion 14 of the tang 12 so that the rear edge 41 of the enlarged portion 27 of the slot 26 clears the lip 16 so as to permit the handle 10 to be drawn away from the scalpel blade 20. Withdrawing the tang 12 from the scalpel blade 20 involves sliding the tang 12 rearwardly so that its groove 17 disengages from the narrow portion 39 of the scalpel blade slot 26.

The removal of a scalpel blade 20 from a scalpel handle 10 is a problem that needs to be addressed. Whilst specialized blade removal tools and devices are known in the prior art, one of the problems associated with such tools is that the operation of such known tools typically requires a user to use both their hands for removing the blade 20 from the handle 10. For example, U.S. Pat. No. 5,088,173 describes such a two-handed blade removal tool. The use of two hands for blade removal is considered to be generally unsafe and unreliable. Another problem associated with the prior art tools and devices is that these devices typically include several movable parts. For example, a blade removal tool that incorporates a significant number of moving parts is described in US Patent Publication No. 20150047170A1. The inclusion of a high number of movable parts can make manufacturing of the tool difficult. Another type of blade removal tool is described in international patent publication No. WO2004093706A1 however the tool that is described therein is specifically designed to remove only one blade and then not to be used again and so is impractical in many situations. Another tool for the removal of scalpel blades is described in U.S. Pat. No. 5,875,533 however, the tool that is described therein is able to accommodate only a limited range of scalpel blades and handles. Some of the other problems associated with currently known blade detachment devices relate to reliability of the prior art devices and high rates of failure due to excessive friction and jamming. Therefore, in view of the shortcomings it would be desirable to provide a blade removal tool, device or apparatus which addresses some of the problems known in the prior art.

SUMMARY OF THE INVENTION

In one aspect, the invention provides an apparatus for detaching a blade from a scalpel handle, the blade having a cutting portion and a heel portion, said blade being removably mounted on a tang provided on the scalpel handle, said apparatus comprising:
 a flexible blade detachment member having a stepped portion for engaging the heel of the blade and a leading angled portion; and
 a backing member;
 the detachment member being arranged adjacent the backing member such that during use the detachment member flexes in only one direction, away from the mounting tang in response to force applied by the handle to the leading angled portion thereby causing the blade and the handle to be separated and detached relative to each other wherein upon exerting a manual force for withdrawing the tang from the opening, the stepped portion engages the heel of the blade resulting in detachment of the blade from the tang.

In an embodiment, the apparatus further comprises a backing plate arranged for constraining the flexing direction of the detachment member.

In an embodiment, the detachment member defines an opening, preferably in the form of a tang receiving slot. Preferably, the opening extends between a proximal end and a distal end, the opening being provided for receiving the tang therein and positioning the mounted blade adjacent an underside of the detachment member.

In an embodiment, the detachment member further comprises a spacing portion for separating the heel of the blade from a shoulder portion connecting the tang with the handle, the spacing portion being shaped for insertion in between the heel of the blade and the shoulder portion.

In an embodiment, the spacing portion is shaped such that insertion of the tang into the opening results in insertion of the spacing portion in between the blade and the tang.

In an embodiment, the spacing portion is shaped such that gradual insertion of the tang along a length of the opening results in a corresponding increase in the spacing in between the tang and the heel portion of the blade.

In an embodiment, insertion of the tang into opening results in flexing of the spacing portion in a direction away from the tang thereby increasing the spacing between the tang and the heel portion of the blade.

Preferably, gradual insertion of the tang from the proximal end to the distal end of the opening results in positioning of the spacing portion in between the tang and the blade.

In an embodiment, upon insertion of the tang into the opening, at least a part of the scalpel handle is positioned in between the detachment member and the heel of the blade thereby applying a flexing force upon the detachment member resulting in the flexing of the detachment member (which is constrained by the backing member). During use, a flexing force is generated when the shoulder portion presses upon the detachment member, specifically the spacing portion of the detachment member (which is constrained to flex in a downward direction only) resulting in the downward flexing of the spacing portion of the detachment member.

In an embodiment, the spacing portion comprises two mutually opposed surfaces. When the spacing portion is positioned in between the shoulder portion and the heel of the blade, one of said mutually opposed surfaces is adapted for engaging the heel of the blade; and the other of the mutually opposed surfaces is adapted for engaging the shoulder.

In an embodiment, the spacing portion comprises a convergent configuration such that the spacing portion preferably converges generally in a direction towards the proximal end of the opening. Preferably, the spacing portion comprises a triangular cross section.

In an embodiment, the stepped portion is positioned across a length of the detachment member adjacent said spacing portion.

Preferably, the stepped portion is formed integrally with the spacing portion.

In an embodiment, the detachment member further comprises a blade engaging portion, the blade engaging portion preferably formed integrally with the spacing portion such that during use, upon insertion of the tang into the opening, the blade mounted on the tang engages the blade engaging portion.

Preferably, upon exerting a manual force for pulling the tang out of the opening, the blade abuts the blade engaging portion and the stepped portion engages the heel of the blade resulting in detachment of the blade from the tang.

In an embodiment, the apparatus further comprises a collection chamber positioned below the detachment member for collecting the blade when the blade becomes detached from the scalpel handle.

In an embodiment, the apparatus further comprises a guide, preferably arranged adjacent the proximal end of the opening, for guiding the tang into the opening and positioning the mounted blade along an underside of the detachment member.

In an embodiment, the apparatus further comprises a support, preferably positioned adjacent said guide for supporting at least a part of the scalpel handle during insertion of the tang into the opening.

In an embodiment, the blade detachment member and the backing plate are arranged relative to a supporting panel preferably positioned above a collection chamber.

In an embodiment, the apparatus further comprises a cover, preferably arranged relative to the housing, said cover being operable for allowing access to the opening defined by the backing plate.

In an embodiment, the apparatus further comprises a mounting arrangement for mounting the blade detachment member and the backing plate relative to a mounting surface.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Referring to FIGS. 2 to 7, a first embodiment of the present invention in the form of a blade removal device 100 is illustrated. The blade removal device 100 comprises a flexible blade detachment member 110 (preferably comprising a flexible polymeric material) that is arranged alongside a rigid polymeric backing plate 120. Specifically, the backing plate 120 is contiguously positioned above the flexible blade detachment member 110 in order to constrain the flexing of the blade detachment member 110 and only allow downward flexing of the detachment member 110 during use.

Figure 3:
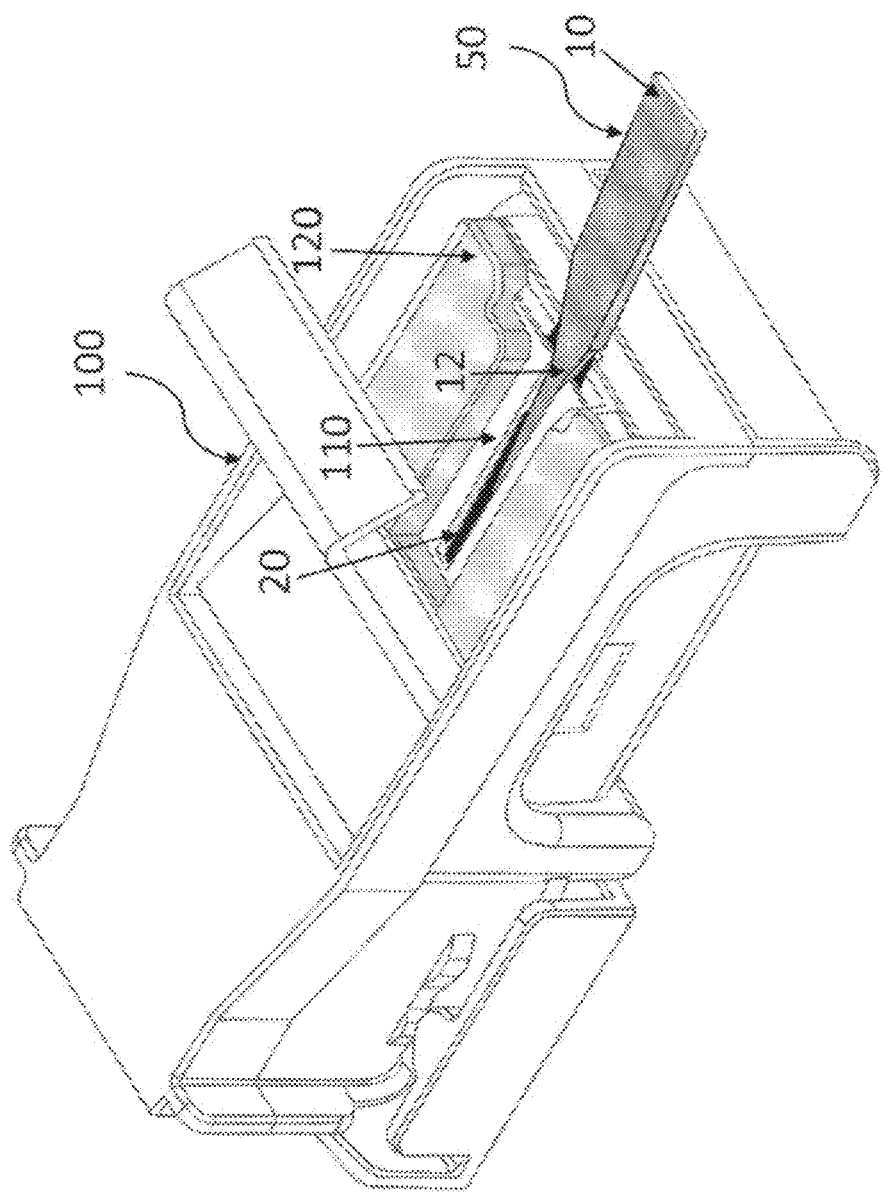
FIGS. 3 and 3a are top perspective views of the blade removal device 100 whereby parts of the surgical knife 50, namely the tang 12 and the mounted blade 20 are in engagement with the blade removal device 100.
Figure 3A:
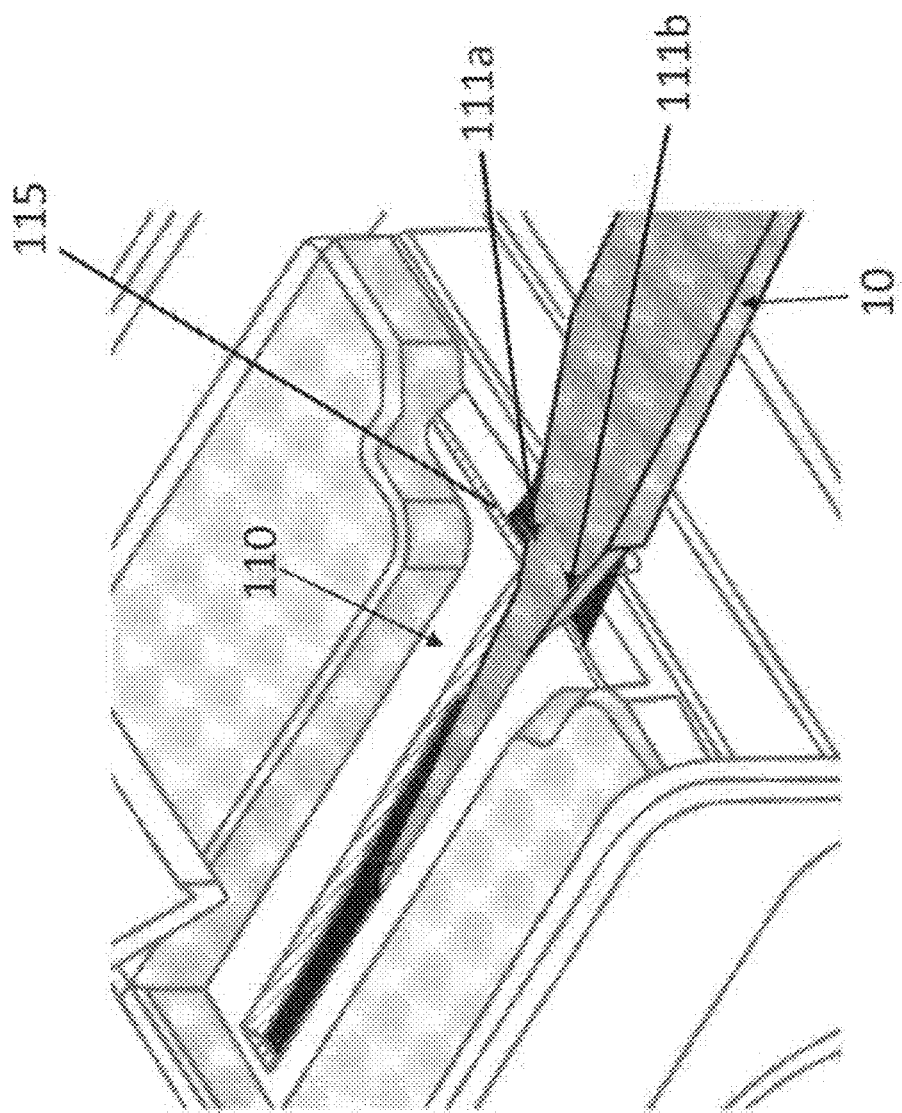
Figure 4:
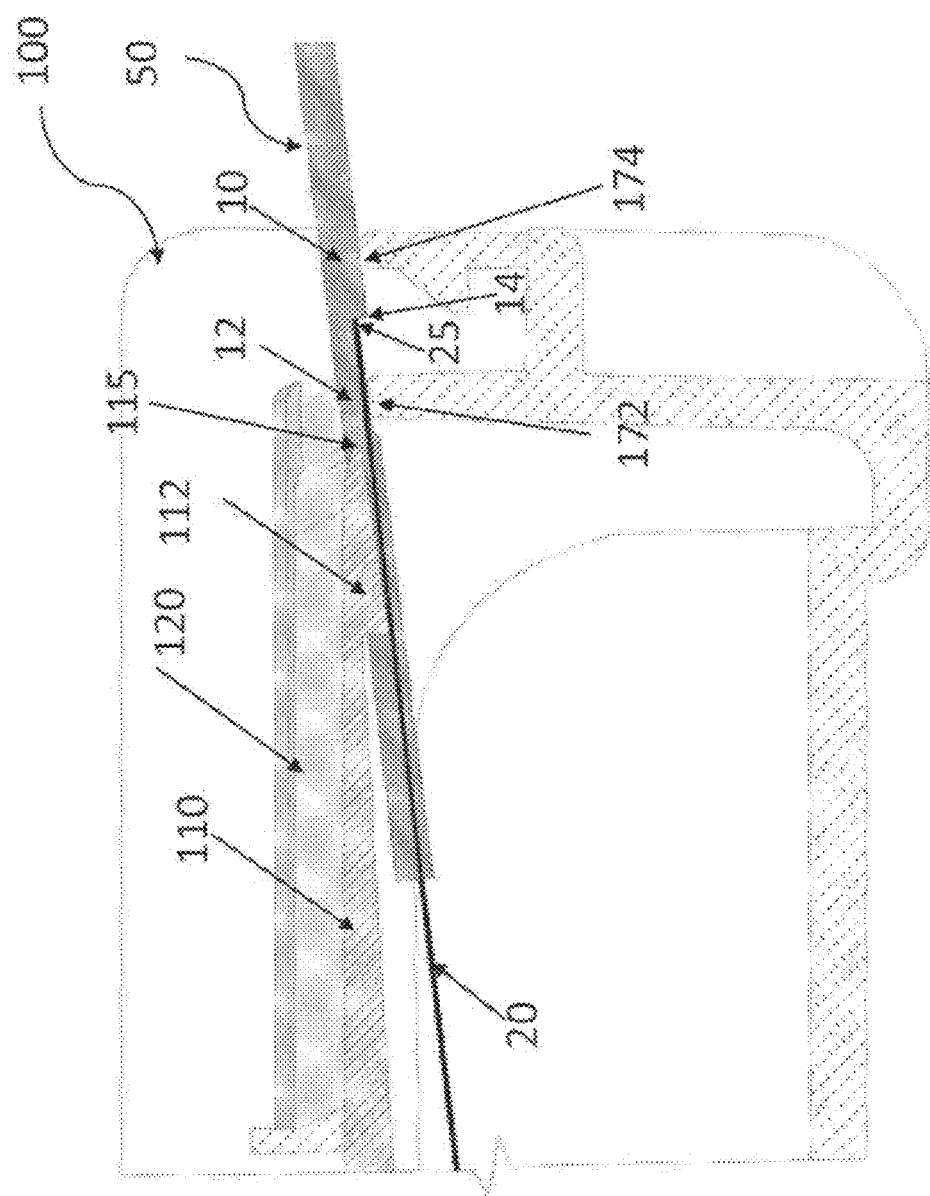
FIGS. 4 and 4a are sectional views of the blade removal device 100 whereby the surgical knife 50 is shown in an initial inserted configuration.
Figure 4A:
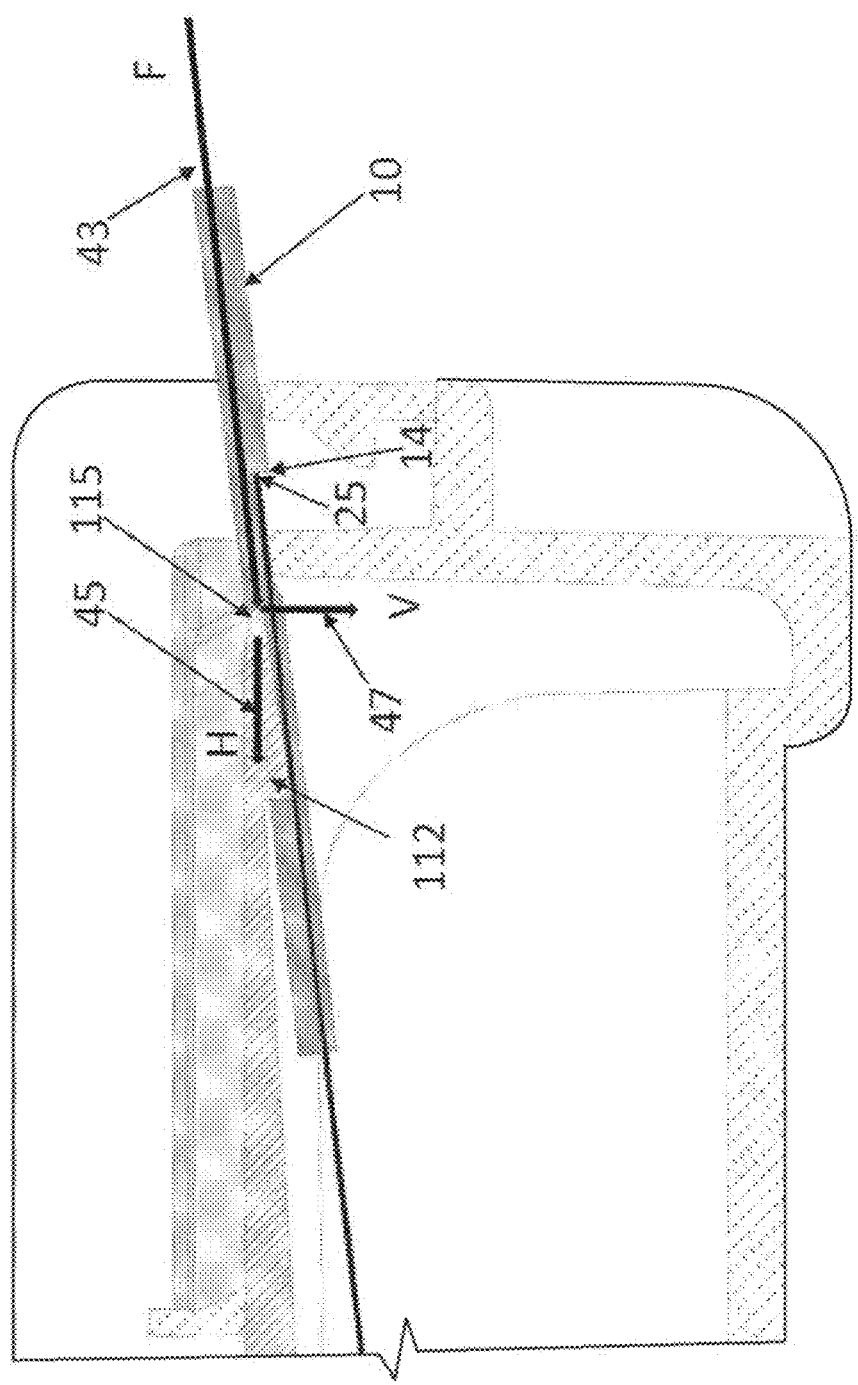

The detachment member 110 is formed with a longitudinal opening 130 that extends between a leading end 132 and a trailing end 134. The opening 130 is wide enough for the tang 12 to pass through but sufficiently narrow to obstruct passage of the blade 20. The opening or slot 130 is defined by the detachment member 110 and is shaped for positioning the tang 12 within the opening 130 which results in the mounted blade 20 being positioned adjacent an underside portion of the detachment member 110, as best shown in FIGS. 3, 3a and 4. The backing plate 120 is formed with a backing plate slot 122 that is wider than the detachment member opening 130. The backing plate slot 122 extends about the opening 130 to accommodate the width of the handle 10 as the tang 12 is received in the opening 130. The backing plate slot 122 is sized to receive handles of varying sizes including larger handles. A guiding arrangement 170 is also provided for guiding the tang 12 into the opening 130. Specifically, spaced apart guiding supports 172 and 174 (identified in FIG. 4) are provided for supporting and guiding the tang 12 into the opening 130. As shown particularly clearly in FIGS. 3a to 5, the rearwardly diverging sides 111a, 111b of the shoulder 14 generate frictional forces against the leading end 115 of the detachment member 110 when the handle 10 is pushed into the opening 130 at a slight inclination in a downward direction as shown in FIG. 4A.

The detachment member 110 further comprises a spacing portion 112 for separating the heel 25 of the blade 20 from the tang 12. The spacing portion 112 comprises a substantially triangular or convergent cross section which converges to a leading angled portion in the form of an angular tip 115 that assists the spacing portion 112 to become positioned in between the heel 25 of the blade 20 and the tang 12 when the tang 12 is inserted into the opening 130. Therefore, gradual insertion of the tang 12 into the opening 130 results in the shoulder 14 pushing the spacing portion 112 (which is restrained by the backing plate 120) which causes the spacing portion 112 to flex in a downward direction due to the angular tip 115. The flexing of the spacing portion 112 brings the heel 25 of the blade 20 away from the shoulder 14 which eventually results in the spacing portion 112 becoming wedged in between the shoulder 14 and the heel portion 25 of the blade 20 as shown in FIG. 4. Referring to FIG. 4a in particular, the force F (item 43) used to push in the handle is at a slight incline. The pushing force F (item 43) is resolved by the angular tip 115 into a horizontal component H (item 45) (the force that moves the scalpel handle 10) and a vertical force V (item 47) (which is the force that flexes the spacing portion downward). As explained in the earlier sections, the contiguous arrangement of the backing plate 120 adjacent the detachment member 110 ensures that the spacing portion 112 always flex in one direction.

Figure 5:
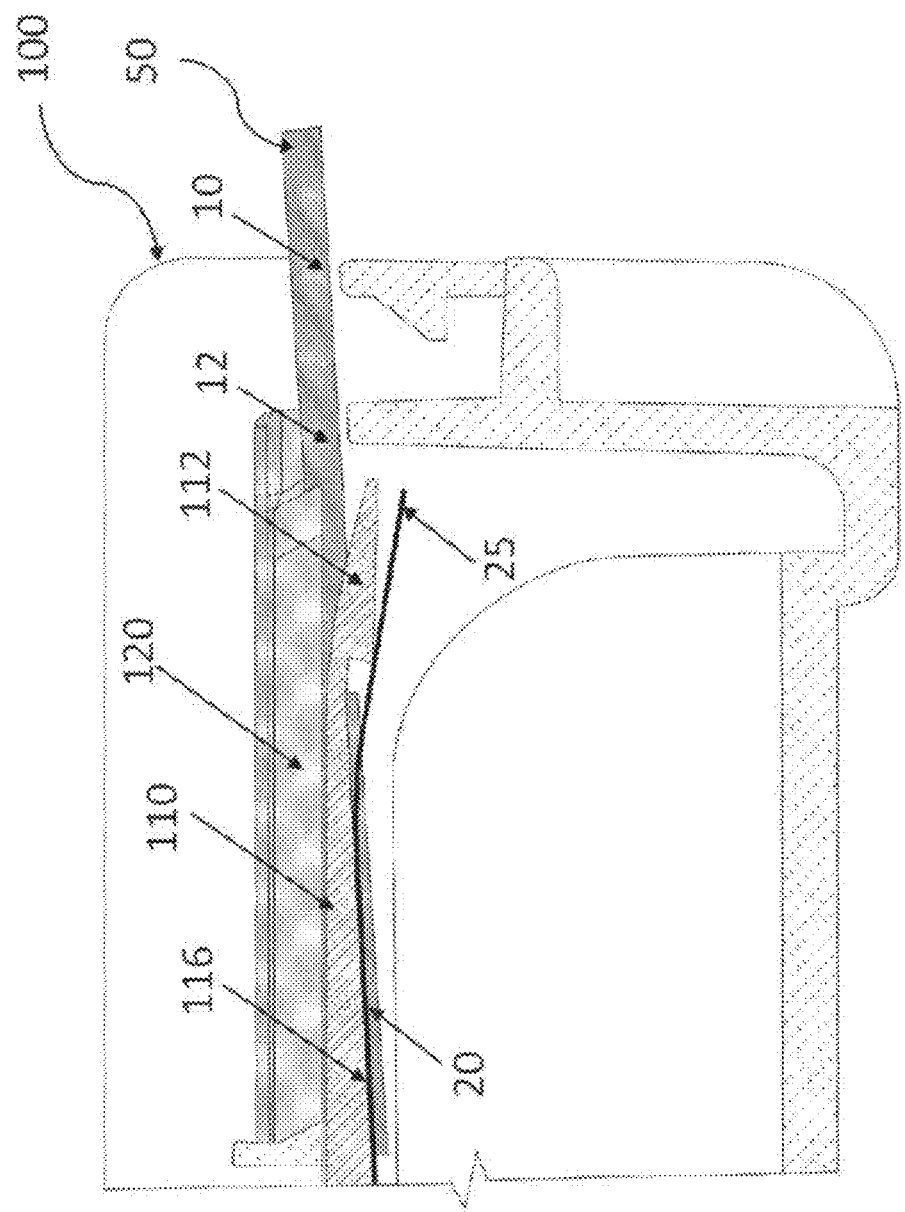
FIG. 5 is a sectional view of the blade removal device 100 whereby the surgical knife 50 is shown in an intermediate inserted configuration.

Further insertion of the tang 12 into the opening 130 results in the spacing portion 112 becoming positioned in between the heel portion 25 of the blade 20 and the shoulder 14 of the scalpel handle 10. The positioning of the triangular spacing portion 112 by the initial insertion or pushing of the tang 12 into the opening 130 results in a downward flexing force V 47, being applied on the spacing portion 112 whilst the tang proceeds along the opening 130 due to horizontal force H 45. Any tendency for upward flexing of the spacing portion 112 is restricted due to contiguous arrangement of the backing plate 120 as a result of which flexing of the spacing portion 112 is limited in the downward direction. The flexing of the spacing portion 112 also results in the heel 25 of the blade 20 being brought away from the shoulder portion 14 and becoming spaced apart from the shoulder 14 The bringing away of the heel 25 results in the spacing portion 112 eventually becoming wedged in between shoulder 14 and the heel 25. The positioning of the backing plate 120 to constrain or restrict the movement of the detachment member 110, specifically the spacing portion 112 also prevents the tang 12 and the handle 10 from inadvertently becoming lodged under the spacing portion 112 resulting in failure of the blade detachment device 100. The flexing of the spacing portion 112 in a downwardly direction away from the tang 12 is best illustrated in FIG. 5. It is important to note that the contiguous positioning of the backing plate 120 constrains the flexing of the spacing portion 112 in one direction only. Referring particularly to FIG. 5, it is important to note that even though, the heel portion 25 of the blade 20 becomes detached from the shoulder 14 of the tang 12, the shank 23 of the blade 20 which defines the blade slot remains attached to the tang's grooves in this configuration. It is also important to note that upon being flexed, the spacing portion 112 extends beyond the plane of the tang 12. The attachment of the shank 23 of the blade 20 with the tang's grooves in combination with the convergent configuration of the spacing portion 112 results in the heel portion 25 becoming positively biased in a direction towards the shoulder 14.

Figure 6:
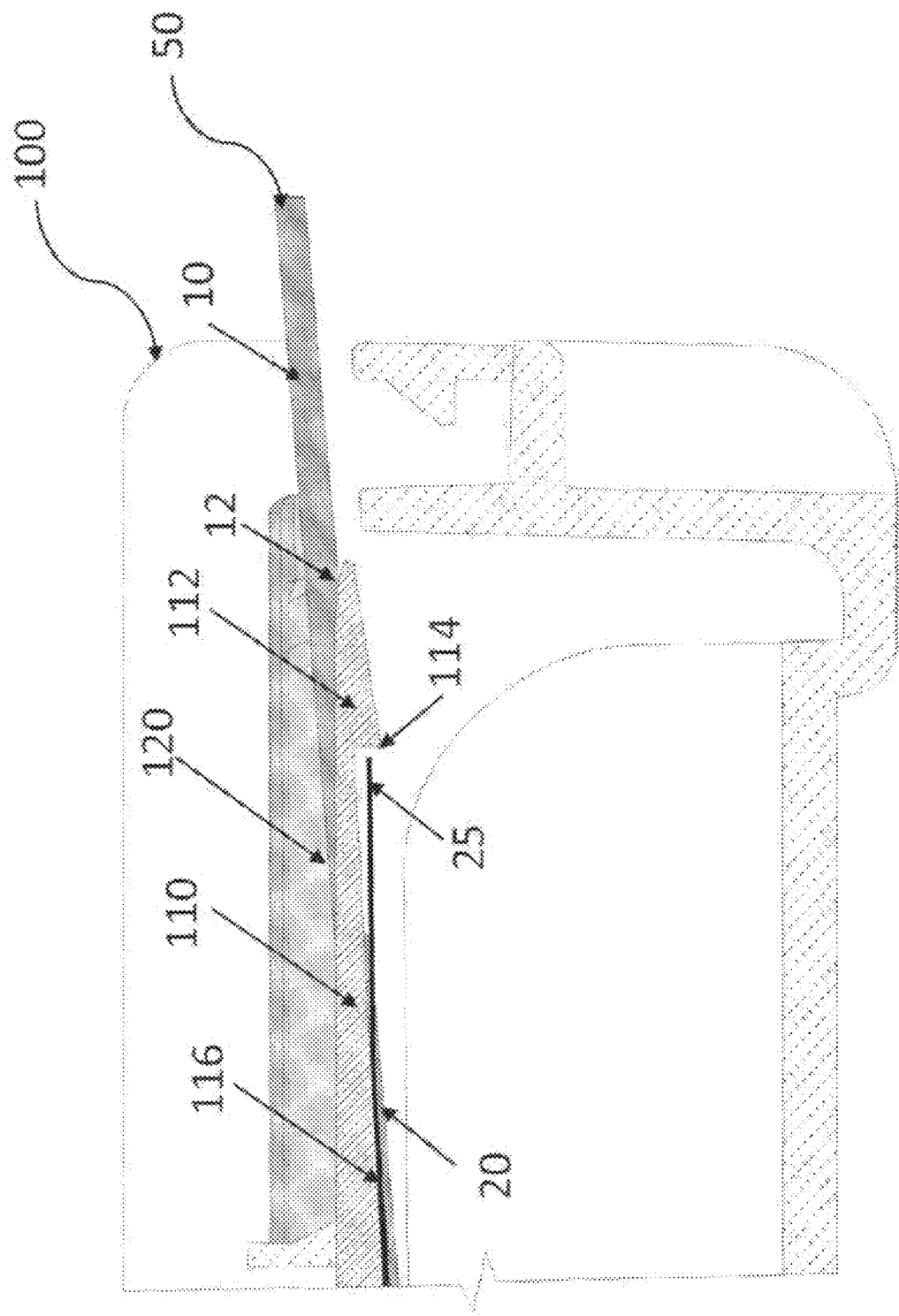
FIG. 6 is a sectional view of the blade removal device 100 whereby the surgical knife 50 is shown in a fully inserted configuration.

Referring to FIG. 6, when the tang 12 is inserted further so that the tang 12 is positioned along the entire length of the opening 130 in a fully inserted position the heel portion 25 of the blade 20 slides past the spacing portion 112 and over a stepped portion 114 of the detachment member 110 to become positioned in abutment with the blade engaging portion 116. The positive bias on the blade 20 due to the positioning of the spacing portion 112 (shown in FIG. 5) provides a pushing force to snap the heel portion 25 behind the stepped portion 114 of the detachment member 110. Once again, it is important to note that the shank 23 of the blade 20 which defines the blade slot remains attached to the tang's grooves 17 in this configuration shown in FIG. 6.

Upon withdrawal of the tang 12 from the opening 130, a pulling force is also applied upon the blade 20 which remains attached to tang's grooves 17 (shank 23 is attached to the tang's grooves 17). However, during the withdrawal of the tang 12 (which involves manual pulling of the handle 10) the blade 20 also undergoes an initial movement which results in the abutment of the heel 25 of the blade 20 with the stepped portion 114 of detachment member 12. Even in the fully inserted position, the shank 23 of the blade 20 is partially brought out of the tang's grooves due to lifting of the heel 25 relative to the shoulder 14. The raised profile of the stepped portion 114 functions as a stop member and prevents the blade 20 from being withdrawn any further even when manual pulling force is applied upon the tang 12 by way of a user pulling the handle 10 out of the opening 130. As a result of the abutment of the stepped portion 114 with the heel portion of the blade 20, the tang 12 is gradually withdrawn out of the blade slot when the manual pulling force continues to be applied by the user. In this configuration, the stepped member 114 functions as a catcher for catching the blade 20 when the tang 12 is withdrawn out of the opening 130. Once the blade 20 becomes completely detached from the tang 12, the detached blade 20 falls into a collection chamber 160.

Figure 1A:
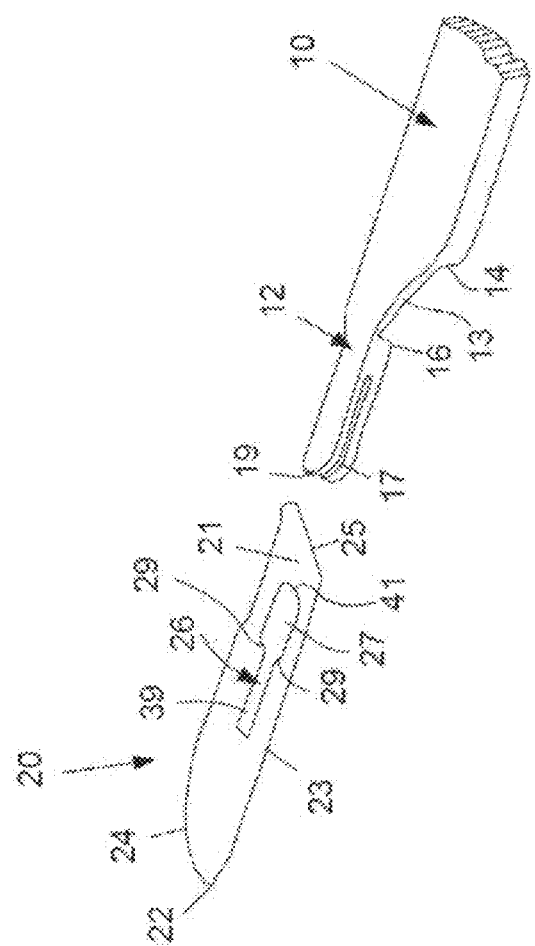
FIGS. 1 and 1A are perspective views of a surgical knife 50 known in the prior art.
Figure 1:
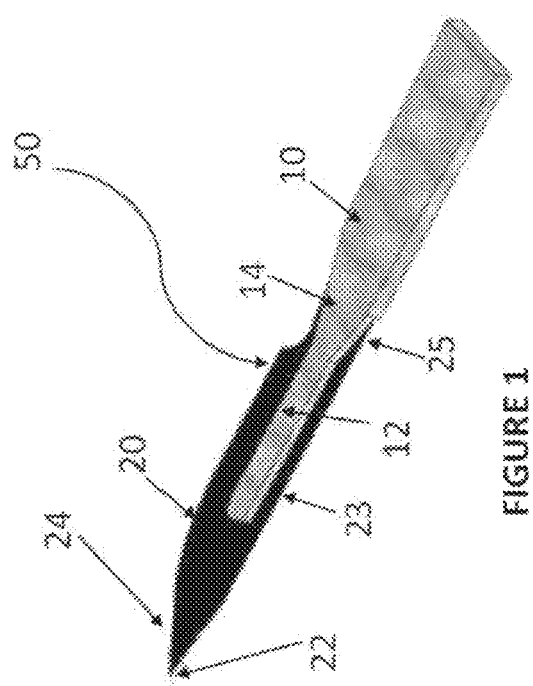
Figure 2:
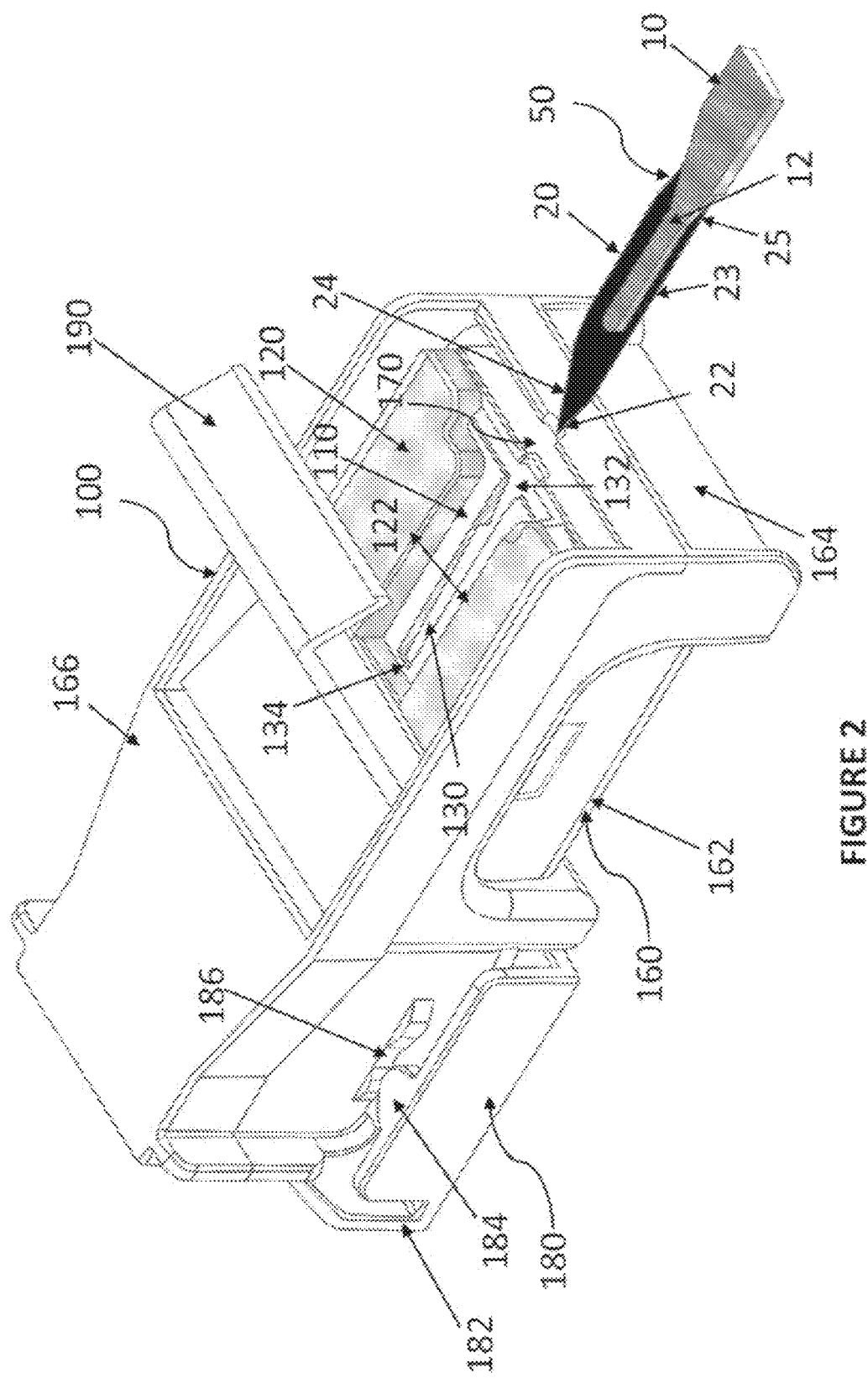
FIG. 2 is a top perspective view of a blade removal device 100 in accordance with a first embodiment of the present invention.
Figure 7:
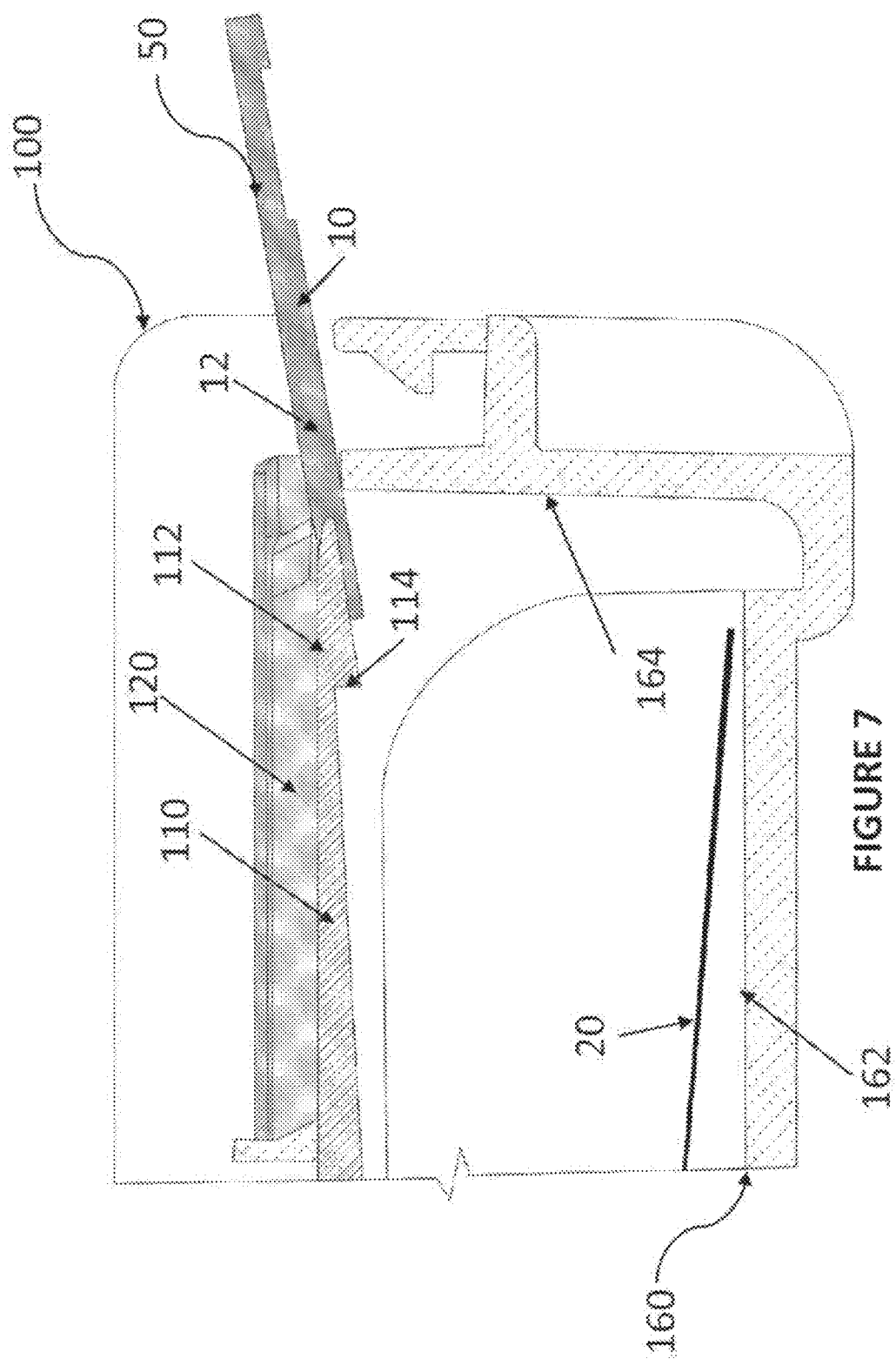
FIG. 7 is a sectional view of the blade removal device 100 whereby the surgical knife 50 is shown in a withdrawn configuration whereby the blade 20 is detached from tang 12.

Referring to FIGS. 1, 2 and 7, the collection chamber 160 may be provided in the form of an open top container comprising a base 162 and upstanding walls 164 defining an internal volume of the collection chamber 160. The blade removal device 100 may be positioned substantially above the upstanding walls 164 of the collection chamber 160. As shown in FIGS. 1 and 2, the blade removal device 100 may be fastened onto a top panel 166 which may be positioned above the collection chamber 160. A hingedly attached cover flap 190 is also provided for allowing access to the opening 130. A mounting arrangement 180 is also provided for placing the blade removal device 10 upon a mounting surface. The mounting arrangement 180 comprises a mounting bracket 182 defining a cradle for receiving the base 162. Outwardly extending projections 184 in the mounting bracket 182 are configured for attachment to projection receiving portions 186 provided along the side walls 164 for releasably fastening the collection chamber 160 (and the blade removal device 100 mounted upon the top panel 166) to the mounting bracket 182. The blade removal device 100 shown in FIGS. 2 to 7 is positioned or oriented to allow sideways insertion of the tang 12 into the opening 130 in a substantially horizontal configuration.

Referring to FIGS. 8 to 14, a second embodiment of the present invention in the form of a blade removal device 200 is illustrated. The blade removal device 200 comprises a flexible blade detachment member 210 (preferably comprising a resilient polymeric material) that is arranged alongside a backing plate 220. Specifically, the backing plate 220 is positioned alongside the flexible blade detachment member 210 in a substantially parallel arrangement in order to constrain the flexing of the blade detachment member 210 and only allow downward flexing of the detachment member 210 during use.

Figure 10:
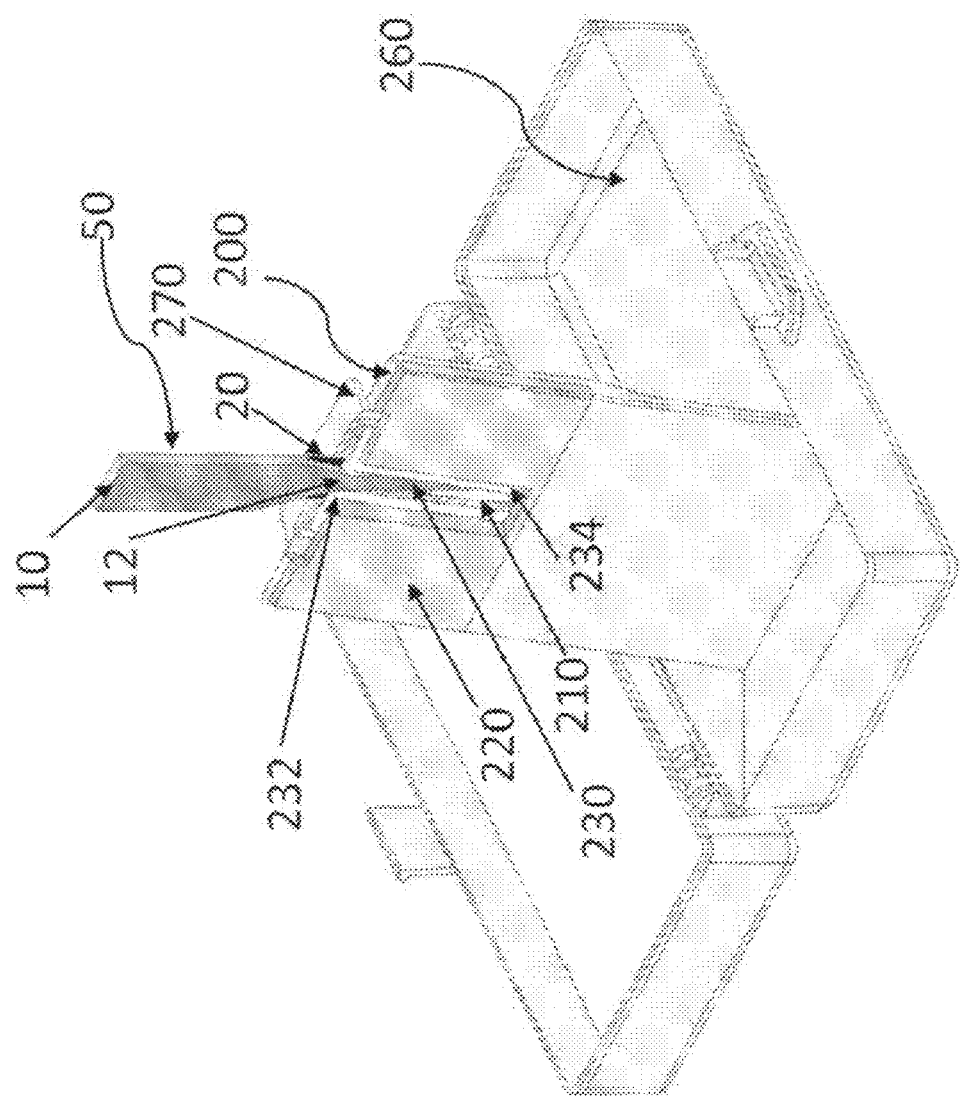
FIG. 10 is a top perspective view of the blade removal device 200 whereby parts of the surgical knife 50 is illustrated in an initially inserted configuration.
Figure 11:
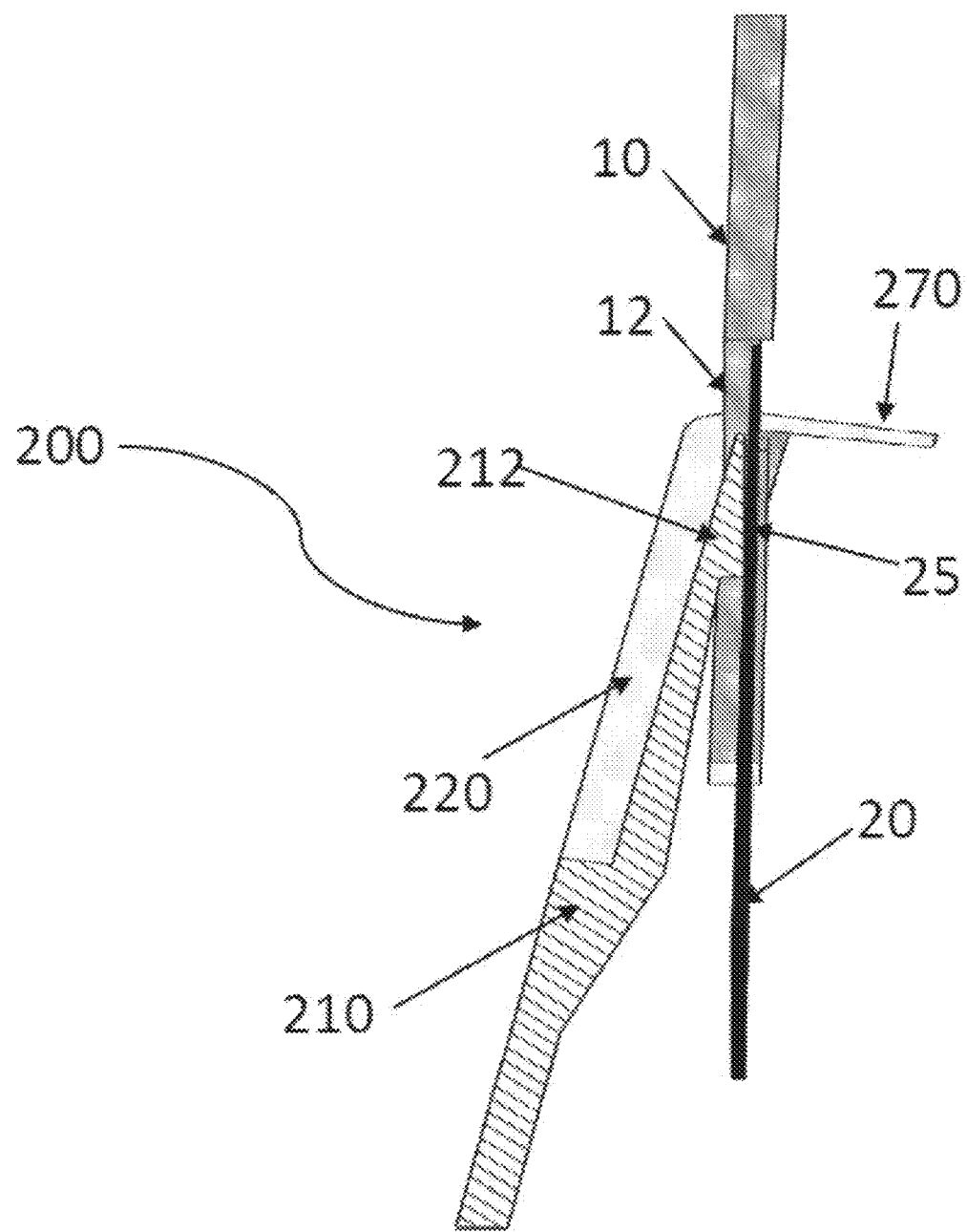
FIG. 11 is a sectional view of the blade removal device 200 whereby the surgical knife 50 is shown in an initial inserted configuration.

The detachment member 210 defines an opening 230 that extends between a proximal end 232 and a distal end 234. The opening 230 is shaped for receiving the surgical blade 50, specifically the tang 12 of the handle 10. The opening or slot 230 is defined by the detachment member 230 and is shaped for positioning the tang 12 within the opening 230 which results in the mounted blade 20 being positioned adjacent below the detachment member 210, as best shown in FIGS. 10 and 11. A guiding arrangement 270 is also provided for guiding the tang 12 into the opening 230 during use.

Unlike the opening 130 in the blade removal device 100 (illustrated in FIGS. 1 to 7), the opening 230 is generally oriented in a transverse upstanding configuration which allows the blade 20, specifically the leading end of the blade 20 to be inserted into the opening 230 in a generally downwardly direction.

Referring to FIGS. 11 to 14, the detachment member 210 further comprises a spacing portion 212 for separating the heel 25 of the blade 20 from the tang 12. The spacing portion 212 comprises a substantially triangular or convergent cross section which allows the spacing portion 212 to become positioned in between the heel 25 of the blade 20 and the shoulder 14 when the tang 12 is initially inserted into the opening 230. Gradual insertion of the tang 12 into the opening 230 results in the shoulder 14 pushing the spacing portion 212 (which is restrained by the backing plate 120) which causes the spacing portion 212 to flex in a downward direction. The flexing of the spacing portion 212 lifts the heel 25 of the blade 20 which eventually results in the spacing portion 212 becoming wedged in between the shoulder 14 and the heel portion 25 of the blade 20 as shown in FIG. 11.

Figure 12:
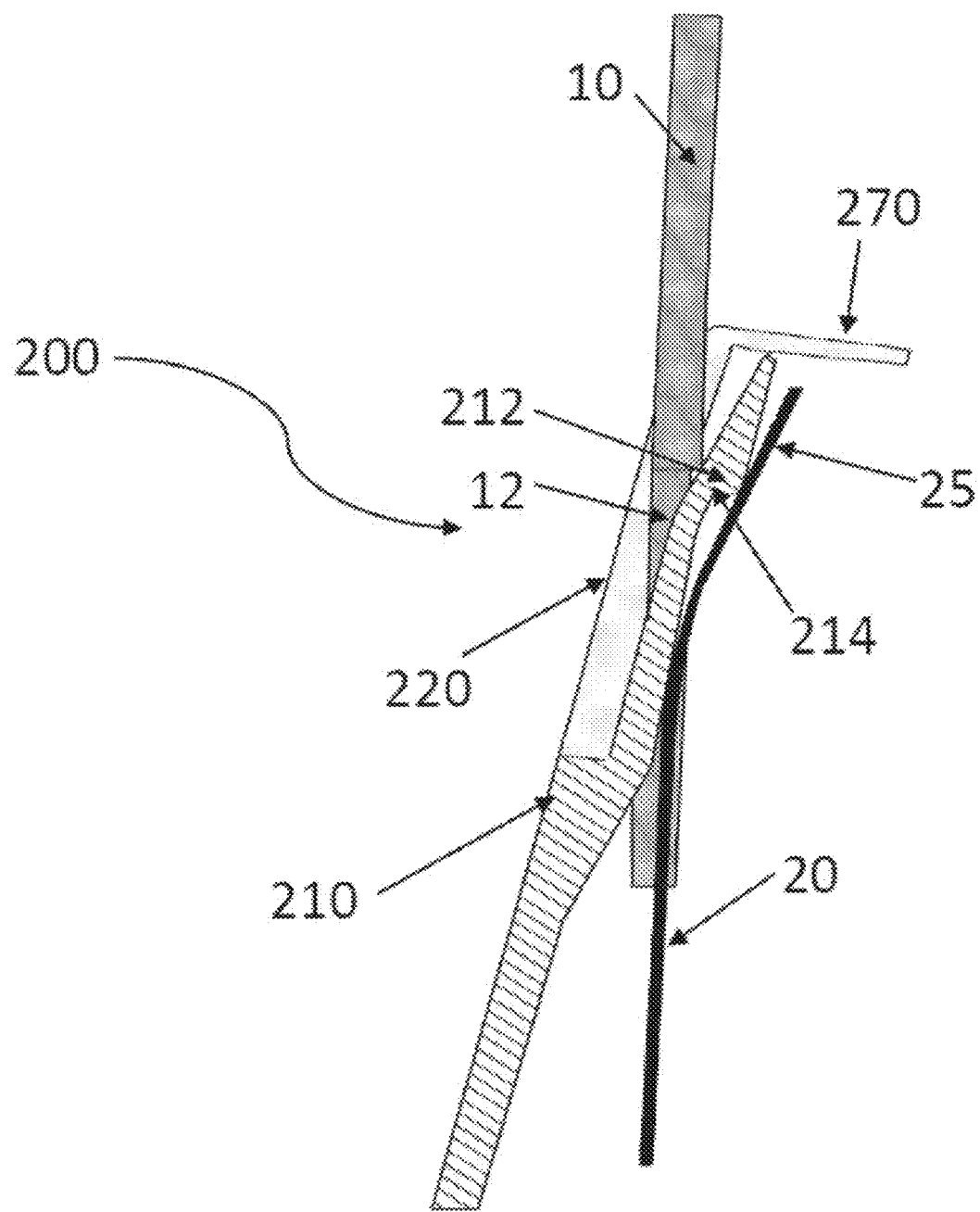
FIG. 12 is a sectional view of the blade removal device 200 whereby the surgical knife 50 is shown in an intermediate inserted configuration.

Further insertion of the tang 12 into the opening 230 results in the spacing portion 212 becoming completely positioned in between the heel portion 25 of the blade 20 and the and the shoulder 14 of the scalpel handle 10. The positioning of the triangular spacing portion 212 by the initial insertion or pushing of the tang 12 into the opening 230 results in a downward flexing force on the spacing portion 212. The upward flexing of the spacing portion 212 is restricted due to contiguous arrangement of the backing plate 220 as a result of which flexing of the spacing portion 212 is limited in the downward direction. The flexing of the spacing portion 212 also results in the heel 25 of the blade 20 lifting away from the shoulder portion 14 and becoming spaced apart from the shoulder 14 The lifting of the heel 25 results in the spacing portion 212 eventually becoming wedged in between shoulder 14 and the heel 25. The positioning of the backing plate 220 to constrain or restrict the movement of the detachment member 210, specifically the spacing portion 212 also prevents the tang 12 and the handle 10 from inadvertently becoming lodged under the spacing portion 212 resulting in failure of the blade detachment device 200. The flexing of the spacing portion 212 in an outwardly direction away from the shoulder 14 and the backing plate 220 is illustrated in FIG. 12. It is important to note that the positioning of the rigid backing plate 220 alongside the detachment member 110 constrains the flexing of the spacing portion 212 in one direction only. Referring particularly to FIG. 12, it is important to note that even though, the heel portion 25 of the blade 20 becomes detached from the shoulder 14 the shank 23 of the blade 20 (which defines a part of the blade slot) remains attached to the tang's grooves in this configuration. It is also important to note that the spacing portion 212 comprises a slightly raised profile and projects beyond the plane of the tang 12 as shown in FIG. 12. The attachment of the shank 23 of the blade 20 with the tang's grooves in combination with the convergent configuration of the spacing portion 212 results in the heel portion 25 becoming positively biased in a direction towards the shoulder 14.

Figure 13:
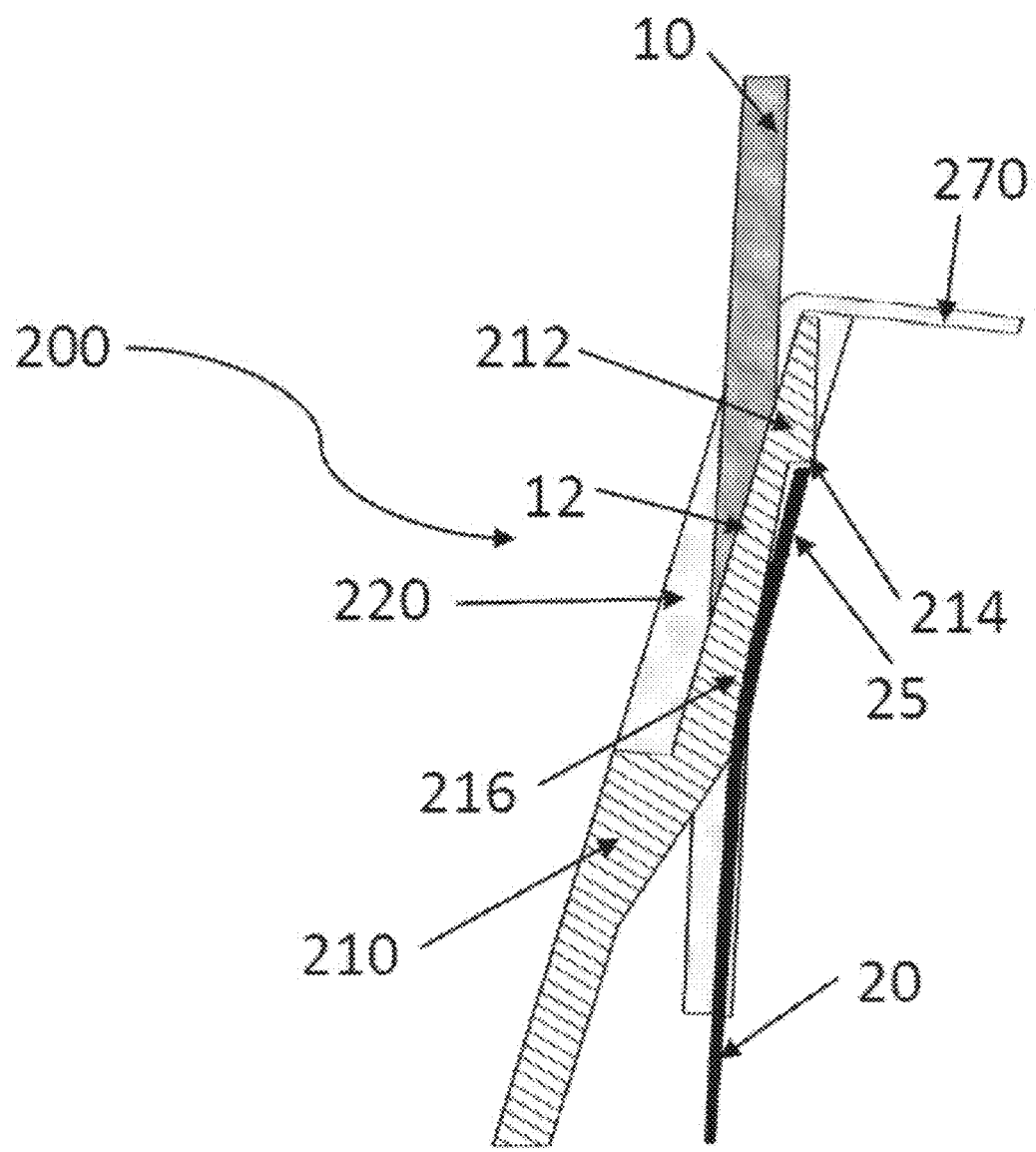
FIG. 13 is a sectional view of the blade removal device 200 whereby the surgical knife 50 is shown in a fully inserted configuration.

Referring to FIG. 13, when the tang 12 is inserted further into the opening 230 so that the tang 12 is positioned along the entire length of the opening 230, the heel portion 25 of the blade 20 slides past the spacing portion 212 and over a stepped portion 214 of the detachment member 210 to become positioned in abutment with the blade engaging portion 216. The positive bias on the blade 20 due to the positioning of the spacing portion 112 (shown in FIG. 12) provides a pushing force to snap or push the heel portion 25 behind the stepped portion 214 of the detachment member 110 (as shown in FIG. 13). Once again, it is important to note that the shank 23 of the blade 20 which defines the blade slot remains attached to the tang's grooves in this configuration shown in FIG. 13.

Upon withdrawal of the tang 12 from the opening 230, an upwardly directed pulling force is also applied upon the handle 10. Specifically, the pulling force is applied upon the tang 12 and the blade 20 which remains attached to at least a forward end of the tang's grooves (shank 23 is attached to the tang's grooves). However, during the withdrawal of the tang 12 (which involves manual pulling of the handle 10) the blade 20 also undergoes an initial movement which results in the abutment of the heel 25 of the blade 20 with the stepped portion 214. The raised profile of the stepped portion 214 functions as a stop member and prevents the blade 20 from being withdrawn any further even when manual pulling force continues to be applied upon the tang 12 by way of a user pulling the handle 10 out of the opening 230. As a result of the abutment of the stepped portion 214 with the heel portion of the blade 20, the tang 12 is gradually withdrawn out of the blade slot of the blade 20 when the manual pulling force continues to be applied by the user. In this configuration, the stepped member 214 functions as a catcher for catching the blade 20 when the tang 12 is withdrawn out of the opening 230. Once the blade 20 becomes completely detached from the tang 12, the detached blade 20 falls into a collection chamber 260 below the blade removal device 200.

Figure 8:
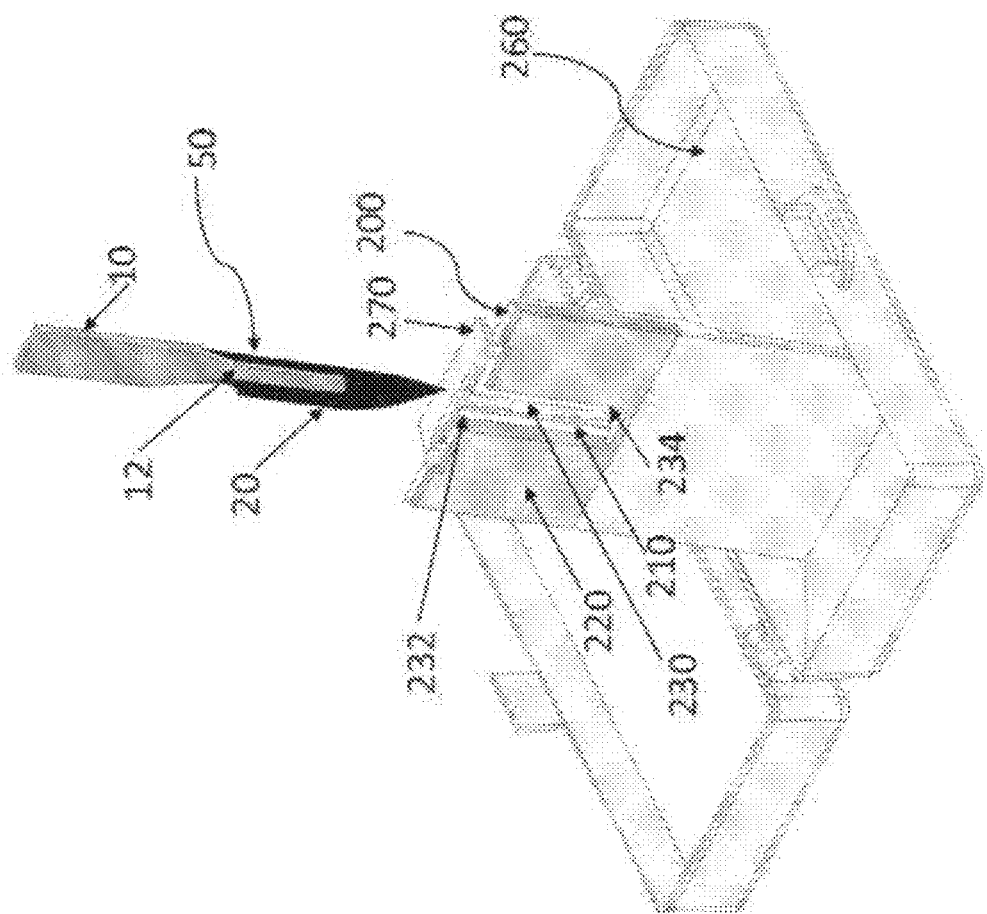
FIG. 8 is a top perspective view of a blade removal device 200 in accordance with a second embodiment of the present invention.
Figure 9:
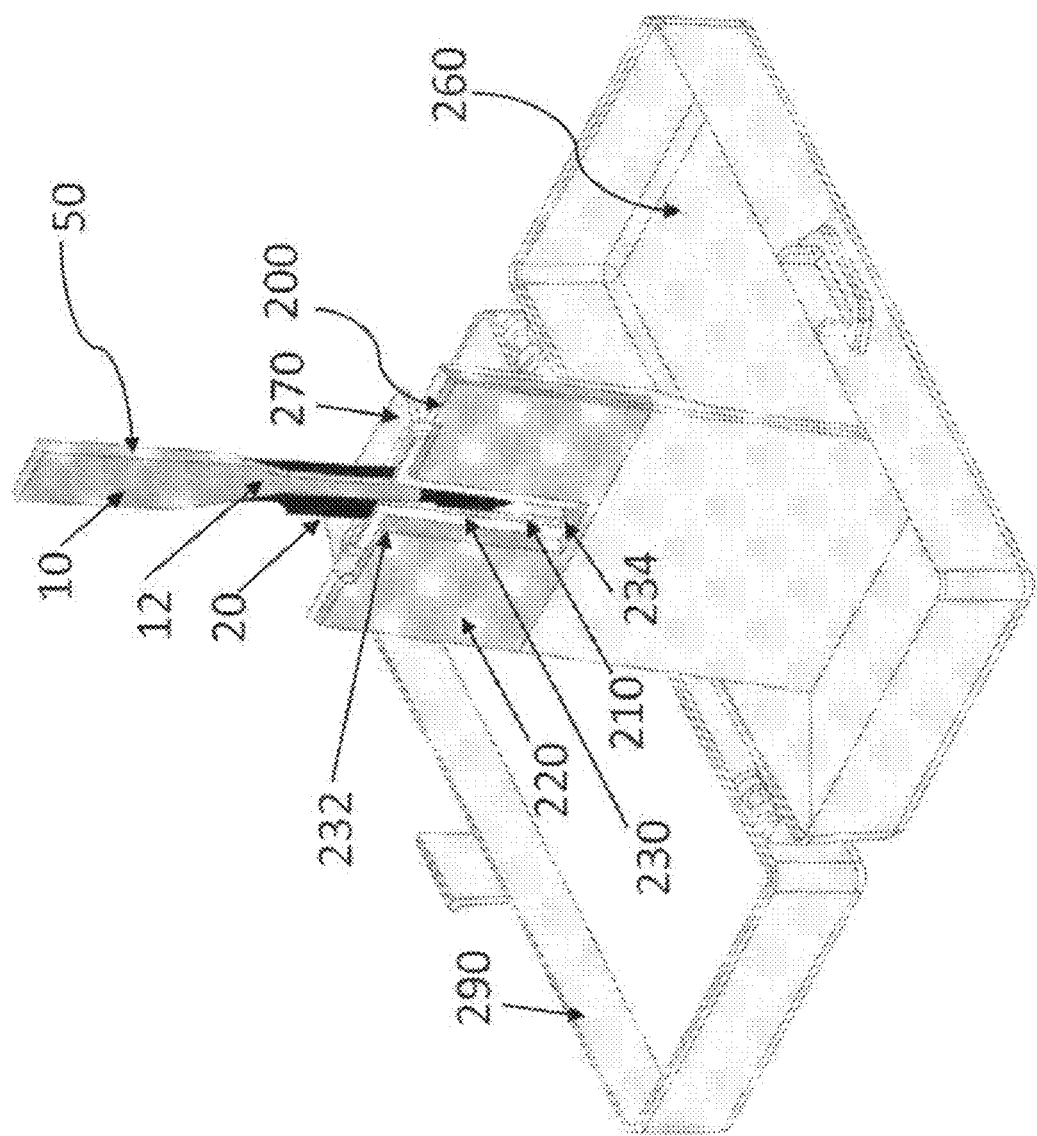
FIG. 9 is a top perspective view of the blade removal device 200 whereby parts of the surgical knife 50, namely the tang 12 and the mounted blade 20 are in engagement with the blade removal device 200. The surgical knife 50 is illustrated in an initially inserted configuration.
Figure 14:
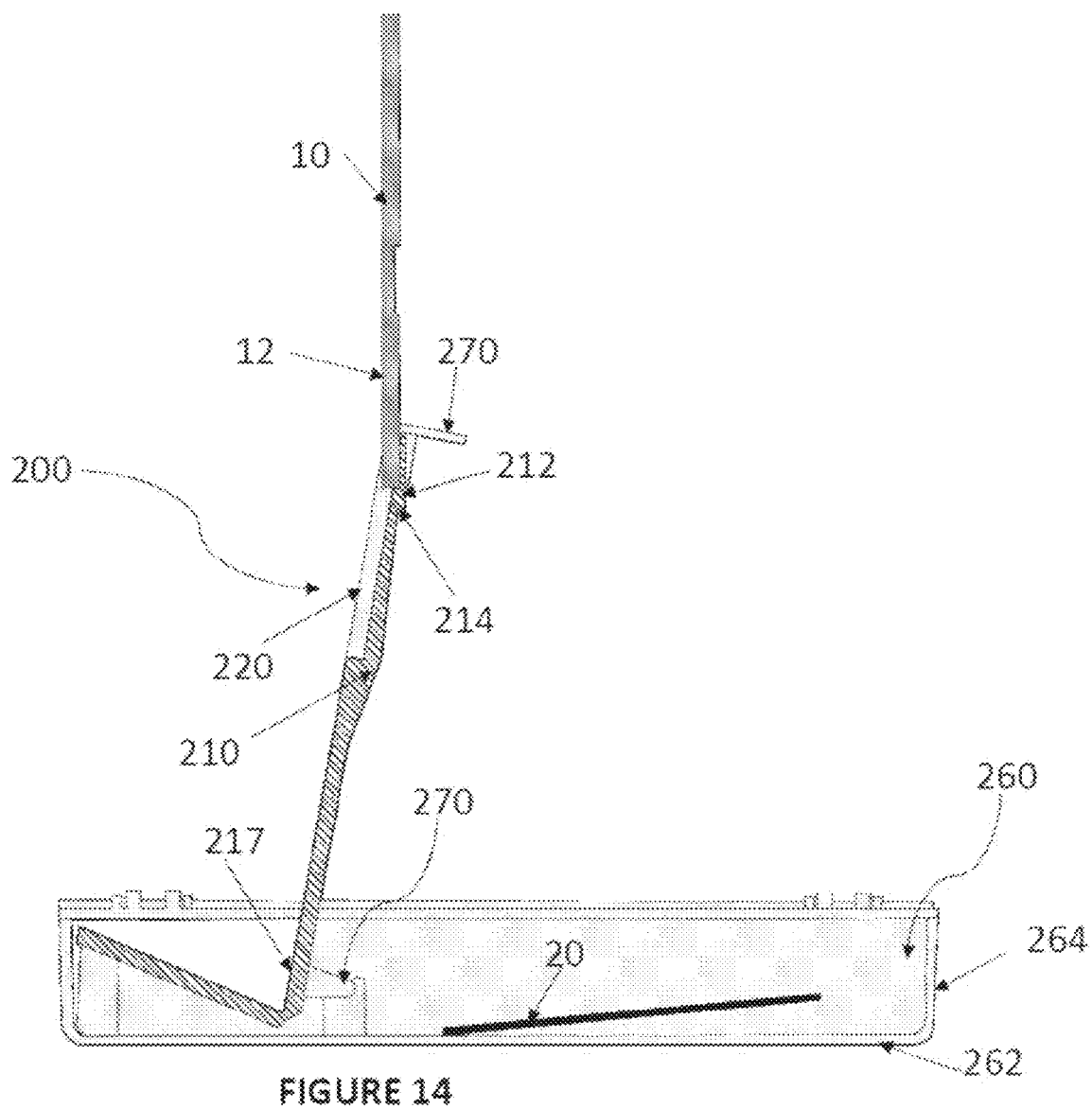
FIG. 14 is a sectional view of the blade removal device 200 whereby the surgical knife 50 is shown in a withdrawn configuration whereby the blade 20 is detached from tang 12.

Referring to FIGS. 8, 9 and 14, the collection chamber 260 may be provided in the form of an open top container comprising a base 262 and upstanding walls 264 defining an internal volume of the collection chamber 260. The blade removal device 200 may be positioned on the base 262 in an upstanding configuration. As shown clearly in FIG. 14, an end portion 217 of the detachment member 210 may pivot relative to the base 260 by way of a pivoting arrangement 270. FIG. 14 illustrates an elevated in-use configuration of the blade removal device 200. The blade removal device 200 may also be pivoted into a lowered position to stow the device 200 and place the device 200 within the confines of the container 260 during periods of non-use. A hingedly attached cover flap 290 is also provided for closing the container 260 when the blade removal device 200 is in a stowed configuration.

In compliance with the statute, the invention has been described in language more or less specific to structural or methodical features. The term "comprises" and its variations, such as "comprising" and "comprised of" is used throughout in an inclusive sense and not to the exclusion of any additional features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Any embodiment of the invention is meant to be illustrative only and is not meant to be limiting to the invention. Therefore, it should be appreciated that various other changes and modifications can be made to any embodiment described without departing from the scope of the invention.

Features, integers, characteristics, or groups described in conjunction with a particular aspect, embodiment or example of the invention are to be understood to be applicable to any other aspect, embodiment or example described herein unless clearly incompatible therewith.

The invention claimed is:

1. An apparatus for detaching a blade from a scalpel handle, the blade having a cutting portion and a heel portion, said blade being removably mounted on a tang provided on the scalpel handle, said apparatus comprising:
   a flexible blade detachment member having a stepped portion for engaging the heel of the blade and a leading angled portion, the detachment member defining an opening in the form of a tang receiving slot extending between a proximal end and a distal end relative to the heel portion of the blade, said opening being provided for receiving the tang therein and positioning the mounted blade adjacent an underside of the detachment member;
   a backing member comprising a backing plate;
   the detachment member being arranged adjacent the backing member, the backing member arranged for constraining a flexing direction of the detachment member such that during use the detachment member flexes in only one direction, away from the mounting tang in response to force applied by the handle to the leading angled portion thereby causing the heel of the blade and being bought away from the handle wherein upon exerting a manual force for withdrawing the tang from the opening, the stepped portion engages the heel of the blade resulting in detachment of the blade from the tang;
   wherein the detachment member comprises a spacing portion for separating the heel of the blade from a shoulder portion connecting the tang with the handle, the spacing portion being shaped for insertion in between the heel of the blade and the shoulder portion.

2. An apparatus according to claim 1, wherein the spacing portion is shaped such that insertion of the tang into the opening results in insertion of the spacing portion in between the blade and the tang.

3. An apparatus according to claim 2, wherein the spacing portion is shaped such that gradual insertion of the tang along a length of the opening results in a corresponding increase in the spacing in between the tang and the heel portion of the blade.

4. An apparatus according to claim 1, arranged so that insertion of the tang into opening results in flexing of the spacing portion in a direction away from the tang thereby increasing the spacing between the tang and the heel portion of the blade.

5. An apparatus according to claim 4, wherein, gradual insertion of the tang from the proximal end to the distal end of the opening results in positioning of the spacing portion in between the tang and the blade.

6. An apparatus according to claim 5, wherein the spacing portion comprises two mutually opposed surfaces whereby upon the spacing portion being positioned in between the shoulder portion and the heel of the blade, one of said mutually opposed surfaces is adapted for engaging the heel of the blade; and the other of the mutually opposed surfaces is adapted for engaging the shoulder.

7. An apparatus according to claim 6, wherein the spacing portion comprises a convergent configuration such that the spacing portion converges in a direction towards the proximal end of the opening.

8. An apparatus according to claim 7, wherein the spacing portion comprises a triangular cross section.

9. An apparatus according to claim 1, wherein a stepped portion is positioned across a length of the detachment member adjacent said spacing portion.

10. An apparatus according to claim 9, wherein the stepped portion is formed integrally with the spacing portion.

11. An apparatus according to claim 9, wherein the detachment member further comprises a blade engaging portion formed integrally with the spacing portion such that during use, upon insertion of the tang into the opening, the blade mounted on the tang engages the blade engaging portion.

12. An apparatus according to claim 1, further comprising a collection chamber positioned below the detachment member for collecting the blade when the blade becomes detached from the scalpel handle.

13. An apparatus according to claim 1, further comprising a guide arranged adjacent a proximal end of the opening, for guiding the tang into the opening and positioning the mounted blade along the underside of the detachment member.

14. An apparatus according to claim 13, the apparatus further comprising a support, preferably positioned adjacent said guide for supporting at least a part of the scalpel handle during insertion of the tang into the opening.

15. An apparatus according to claim 1 wherein the blade detachment member and the backing member are arranged relative to a supporting member to position the blade detachment member and the backing plate above a blade collection chamber.

16. An apparatus according to claim 1 further comprising a housing for retaining the detachment member and the backing member in a spaced relationship relative to a base of the housing.

17. An apparatus in accordance with claim 1 further comprising a cover arranged to allow access to the opening defined by the detachment member.

* * * * *